United States Patent [19]

Matsuda et al.

[11] Patent Number: 4,617,275

[45] Date of Patent: Oct. 14, 1986

[54] REAGENT FOR BLOOD ANALYSIS

[75] Inventors: Noriaki Matsuda, Kakogawa; Etsuro Shinkai, Akashi, both of Japan

[73] Assignee: Toa Medical Electronics Co., Ltd., Kobe, Japan

[21] Appl. No.: 653,861

[22] Filed: Sep. 24, 1984

[30] Foreign Application Priority Data

Sep. 29, 1983 [JP] Japan .................. 58-183995

[51] Int. Cl.⁴ .................. G01N 33/48
[52] U.S. Cl. .................. 436/10; 436/17; 436/18
[58] Field of Search .......... 252/408; 424/2–3; 436/17, 18, 8, 10, 15; 435/2; 422/61

[56] References Cited

U.S. PATENT DOCUMENTS

| 3,519,572 | 7/1970 | Kita | 436/18 |
|---|---|---|---|
| 3,874,852 | 4/1975 | Hamill | 252/408 |
| 4,185,964 | 1/1980 | Lancaster | 436/17 |
| 4,248,634 | 2/1981 | Forester | 436/18 |
| 4,264,470 | 4/1981 | Chastain et al. | 436/17 |
| 4,286,963 | 9/1981 | Ledis et al. | 252/408 |
| 4,346,018 | 8/1982 | Carter et al. | 252/408 |
| 4,485,174 | 11/1984 | Chiang et al. | 436/18 |
| 4,521,518 | 6/1985 | Carter et al. | 436/17 |

Primary Examiner—John F. Terapane
Assistant Examiner—T. J. Wallen
Attorney, Agent, or Firm—Stevens, Davis, Miller & Mosher

[57] ABSTRACT

A reagent for blood analysis comprises, as a lysing reagent for leukocyte count, tetradecyltrimethylammonium bromide and/or hexadecyltrimethylammonium chloride, dodecyltrimethylammonium chloride, and citric acid. This reagent is characterized by showing three-peaks fractionation of leukocytes in measuring by means of an automatic blood-analysis instrument. The lysing reagent is used together with a diluent comprising boric acid buffer solution, ethylenediaminetetraacetic acid and (2-pyridylthio-1-oxide) sodium.

4 Claims, 11 Drawing Figures

REAGENT FOR BLOOD ANALYSIS

BACKGROUND OF THE INVENTION

This invention concerns a reagent for blood analysis especially suitable for use in measurement of leukocyte count in a blood by means of an automatic blood-analysis instrument.

Ingredients of blood are closely related with a whole organization or internal organs of human body. Therefore, analytical data of blood are important as an index of diagnosis or treatment. Especially, leukocytes of blood include many useful informations for diagnosis or treatment of organism, since they show a rapid response to variations of organism conditions.

Up to now, leukocyte classification which is carried out by classifying leukocytes into 5 to 8 kinds and counting them has been practiced as an inspection of leukocytes. However, since this inspection depends on visual count by a microscope, the inspection including pretreatment takes comparatively many hours. Further, the determination of visual count demands the expert.

On the other hand, operations of inspection based on leukocyte classification have been partially automated by introducing the pattern-recognition technology of a computer. However, even if the partial automation is possible, the final determination of the inspection is depended on the expert, and it takes many hours for the inspection. Further, large-sized and expensive instruments are demanded for the inspection.

Recently, the automatic blood-analysis instrument which is equipped with a mechanism for counting blood corpuscles such as leukocyte, red corpuscles, platelets and so on has developed to accomplish simplicity and rapidity of the blood analysis. The blood count is carried out by an electric resistance system as shown in FIG. 6. According to this system, the blood is diluted with a diluent 1, and therefore the blood corpuscles 2 are dispersed in the diluent 1. When negative pressure is added in a detector 3, the dispersed blood corpuscles 2 are sucked in the detector 3 through a small hole 4. In that case, outer and inner sides of the detector 3 are provided with outer and inner electrodes 5, 6, respectively, so that a certain current is flowed from the outer electrode 5 to the inner electrode 6. When the blood corpuscles 2 of which the electric resistance is extremely larger than that of the electrolyte (the diluent 1) are passed through the small hole 4, the resistance between both electrodes is changed. Such a change of resistance is taken out as a signal to count the blood corpuscles such as leukocytes.

Before making leukocyte count by means of the electric resistance system, the blood is diluted to a certain dilution magnification, and a certain amount of a lysing reagent for leukocyte count is added. The lysing reagent solves erythrocytes and cytoplasm of leukocytes, and leaves the nuclei to be counted. The nuclei is passed through the small hole 4 of the detector 4.

However, in the traditional practice for counting leukocytes, since a surface active reagent having the strong lyse-force is used as a lysing reagent, all of leukocytes to be counted arrive at the neighborhood of contraction limit, so that total count only, i.e. one-peak fractionation in size distribution as shown in FIG. 7, has been carried out.

In order to improve the one-peak fractionation and to emphasize the difference of the particle size inherent in leukocytes, the lysing reagent capable of slowing the contraction speed of large particles and rapidly contracting small particles such as lymphoid cells has been developed. This lysing reagent contains, as a main ingredient, dodecyltrimethylammonium chloride and tetradecyltrimethylammonium bromide, and thus accomplishes two-peaks fractionation by means of a blood corpuscle counter. This fractionation if called as a discrimination histogram of the populations of lymphoid and myeloid cells or a leukocyte volume histogram. A pattern of two-peaks fractionation is shown in FIG. 8.

Such a blood analysis practiced by the automatic blood-analysis instrument has an advantage that other measuring items, such as erythrocyte number, hemoglobin amount, hematocrit value, platelet number and so on, as well as leukocyte, can be simultaneously measured in a short time. However with respect to leukocyte count, two-peaks fractionation was unsatisfactory in comparison with the practical 6 items classification. Thus, it has been demanded to raise the fractionation number.

SUMMARY OF THE INVENTION

The present invention relates to a reagent for blood analysis capable of making three-peaks fractionation in an automatic blood-analysis instrument.

This reagent for blood analysis comprises, as a lysing reagent for leukocyte count, tetradecyltrimethylammonium bromide and/or hexadecyltrimethylammonium chloride, dodecyltrimethylammonium chloride and citric acid.

Furthermore, this reagent for blood analysis comprises a combination of a lysing reagent and a diluent; the lysing reagent comprising tetradecyltrimethylammonium bromide and/or hexadecyltrimethylammonium chloride, dodecyltrimethylammonium chloride and citric acid; and the diluent comprising boric acid buffer solution, ethylenediaminetetraacetic acid and (2-pyridylthio-1-oxide)sodium.

DETAILED DESCRIPTION

Figure 1:
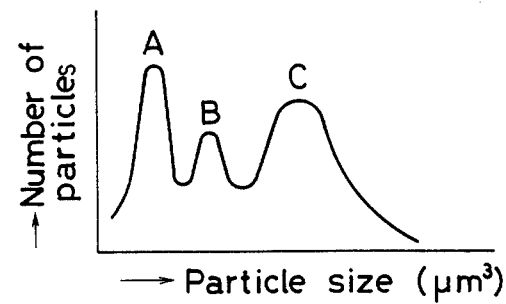
FIG. 1 is a graph showing size distribution fractioned in three peaks.
Figure 8:
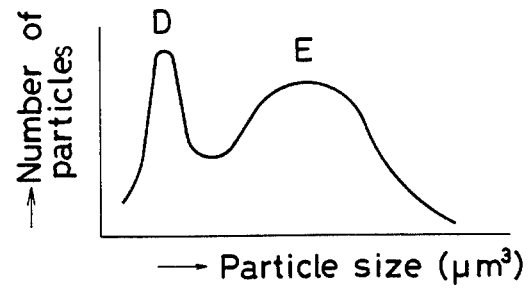

In the present invention, a combination of each quaternary ammonium salt consisting of tetradecytrimethylammonium bromide and/or hexadecyltrimethylammonium chloride, and dodecytrimethylammonium chloride can shrink eosinophils of granulocytes and monocytes in some degree more than lymphocytes in lymphoid/myeloid population, and as a result, forms three-peaks fractionation of leukocytes as shown in FIG. 1. In FIG. 1, Peaks A, B, C indicate normal lymphocytes, eosinophil monocytes and other granulocytes, respectively. In this connection, peak D in two-peaks fractionation shown in FIG. 8 mainly indicates normal lymphocytes, and peak E indicates other components of leukocytes.

One or mixture of the above-mentioned tetradecyltrimethylammonium bromide (hereinafter referred to as "MTAB") and hexadecyltrimethylammonium chloride (hereinafter referred to as "CTAC") are preferably contained in the lysing reagent. In that case, to the aqueous solution in which the above ingredients are solved, citric acid and dodecyltrimethylamonium chloride (hereinafter referred to as "LTAC") are added to form the lysing reagent.

Effect of each ingredient is described below. LTAC can make differences to the contraction rate corresponding to each particle diameter, so that lymphocytes group and granulocytes group are fractionated individually with a large gap, since the contraction effect of LTAC weakens against leulocytes under the suitably arranged concentration. Nevertheless, LTAC has a disadvantage that ghosts of red blood cells are not shrinked, and are admixed with small size cells in lymphocytes. In order to eliminate the disadvantage, citric acid is added. Citric acid is caused to accelating the contraction of membranes (ghosts of red blood cells), and inhibits the aggregation of those.

MTAB has a relatively stronger contraction effect than LTAC. On the other hand, this effect is decreased with the passage of time at a certain range, and thus MTAB can make two-peaks fractionation of lymphocytes and granulocytes. But, since both peaks come into contact with each other, MTAB is used only for one-peak fractionation by itself. Though CTAC has a relatively stronger contraction effect than MTAB, CTAC facilitate appearance of a central peak in three-peaks fractionation due to a tendency that eosinophil granulocytes and monocytes in granular leukocytes are more strongly shrinked.

The preferred compositions of the lysing reagent are described below.

| (Ingredient) | (% by weight) |
|---|---|
| (A) A combination of LTAC and CTAC | |
| LTAC | 26 to 31.5 |
| CTAC | 2.5 to 3.5 |
| Citric acid | 0.01 to 0.02 |
| Water | 61 to 75 |
| Total | 100 |
| (B) A combination of LTAC, MTAB and CTAC | |
| LTAC | 26 to 31.5 |
| MTAB | 1.6 to 2 |
| CTAC | 1.0 to 2 |
| Citric acid | 0.01 to 0.02 |
| Water | 61 to 75 |
| Total | 100 |
| (C) A combination of LTAC and MTAB | |
| LTAC | 26 to 31.5 |
| MTAB | 3 to 4 |
| Citric acid | 0.01 to 0.02 |
| Water | 61 to 75 |
| Total | 100 |

In these combinations (A) to (C), when the amount of LTAC is more than the above range, the lysing reagent produces an insufficient fractionation due to contiguity of each peak of lymphatic leukocytes and other leukocytes. On the other hand, when the amount of LTAC is less than the above range, the lysing reagent produces an insufficient fractionation between lymphatic leukocytes and ghosts of erythrocytes. Also, when the amounts of CTAC nd MTAB to be added are more than the above range, the lysing reagent produces an insufficient fractionation between a group of eosiniphil granulocytes and monocytes and a group of other granulocytes. When the amounts of CTAC, MTAB and citric acid is less than the above range, the lysing reagent produces an insufficient fractionation between lymphocytes and ghosts of erythrocytes.

Figure 2:
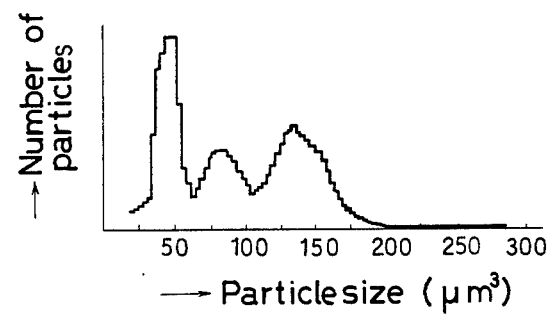
FIG. 2 is a graph showing practically measured size distribution in accordance with the present invention.

A method for making leukocyte count by means of the automatic blood-analysis instrument is described below. The method comprises diluting the gathered blood in a dilute till a certain dilution, which generally is 250 times, adding the lysing reagent, and detecting the size distribution by the electric resistance system mentioned above after 30 to 45 seconds. The lysing reagent is added in the ratio of 1 cc., when 2 cc. of the diluent is added to 0.008 cc. of blood sample. FIG. 2 shows the practical size distribution measured by the above-mentioned method. The size distribution of leukocytes is changed into signals in the detector, and is transmitted through an amplification/discrimination circuits and an interface circuit to a recorder to be recorded by a microcomputer. As an automatic blood-analysis instrument, "MULTI-ITEMS AUTOMATIC BLOOD CORPUSCLE COUNTER CC-800" manufactured by TOA MEDICAL ELECTRONICS CO., LTD. of Japan can be preferably employed. This counter is designed so as to automate pretreatment for arranging sample, which includes diluting step for diluting blood in a high diluted magnification and lysing step for measuring leukocyte and hemoglobin, and can treat and analyze sample at a rate of approximately 80 samples per hour.

Dilution of blood is an important step for preparing sample as well as lysing step, since pH and osmotic pressure of the dilute to be used have a large influence on blood corpuscles in its form and change with the passage of time. Accordingly, the dilute should be arranged to the prescribed pH and osmotic pressure. As to osmotic pressure, the dilute is arranged to an isotonic solution having the prescribed concentration of sodium chloride, and dilutes blood within the range of approximately 200 to 500 times in connection with the items to be measured. Also, pH buffer solution which is added for pH arrangement comprises boric acid and its salt. The conventional dilute which includes phosphoric acid buffer solution is undesirable in view of raising BOD value of waste liquid and resulting in a rich nutrition of the river or the lake.

The dilute is common to each measurement in hemoglobin, leukocyte and erythrocyte, and the dilution is changed every each measurement purpose. In hemoglobin measurement, blood is diluted to 500 times in the dilute. Then, lysing reagent is added to the diluted solution of blood so as to solve erythrocytes sufficiently, and the amount of hemoglobin is measured by a photoelectric colorimeter.

In previous measurement of hemoglobin, the lysing reagent and the dilute to be used has been the same as in leukocyte measurement, and further a cyanic compound has been added to the lysing reagent to change hemoglobin into methemoglobin, i.e. oxidation from $Fe^{230}$ contained in hemoglobin to $Fe^{330}$. However, this method has caused the problem of the treatment of waste liquid including cianide. Therefore, oxyhemoglobin processes has been employed instead of the previous process mentioned above. In oxyhemoglobin process, it is necessary to prevent change of hemoglobin into methemoglobin, since the existance of methemoglobin causes errors in measurement.

According to the present invention, in order to prevent the change of hemoglobin, (2-pyridylthio-1-oxide)-sodium is employed as a preservative in addition to boric acid buffer solution. This compound has the formula:

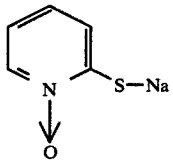

Furthermore, EDTA-2K is used as a chelating reagent together with the above ingredients. Then, all ingredients are solved in a high quality water which is refined by using reverse-osmosis and active carbons. The diluent thus refined has 6 to 8 of pH, and 240 to 310 mOsm/kg. $H_2O$ of osmotic pressure. This diluent is arranged to a certain magnification of dilution in accordance with each measuring item, e.g. 250 times in leukocyte measurement, 500 times in hemoglobin measurement and about 30,000 times in erythrocyte measurement.

The diluent and the lysing reagent in the present invention accomplish the count based on three-peaks fractionation, such as eosinophils, monocytes, lymphocytes and other ingredients. Further, the present invention can prevent generating an environmental pollution due to avoiding cyanide and phosphorus. In addition, the reagent of the present invention facilitate to obtain the valuable and accurate informations concerning blood without taking the larger cost than the conventional operation, together with rapidity and easiness in use of the automatic blood-analysis instrument.

The following Examples are given to illustrate the present invention.

EXAMPLE 1

Leukocyte count of blood taken from patient 1 was measured by "MULTI-ITEMS AUTOMATIC BLOOD CORPUSCLE COUNTER CC-800" mentioned above. In that case, measurement was carried out by electrically resistant detection system. As a pretreatment, 0.08 ml. of blood was diluted to 250 times in 2 ml. of a dilute, and then 1 ml. of a lysing reagent was added to the sample. After 30 seconds, the corpuscles were passed through a small hole provided in the detector.

Figure 3A:
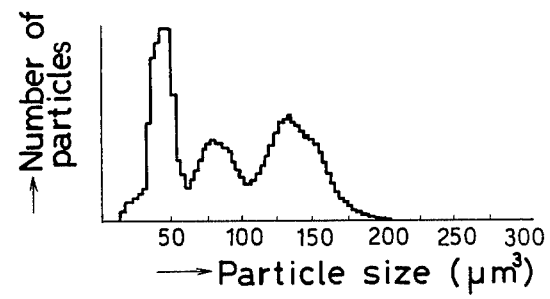
FIGS. 3 (A) and (B) are graphs showing the examination results in Example 2 and Comparative Example 2, respectively.
Figure 3B:
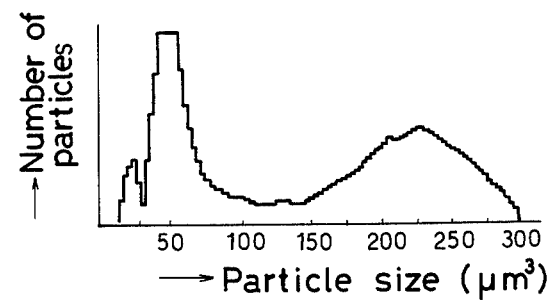

The composition of the lysing reagent employed is an follows:
LTAC—28.5 g
CTAC—3.1 g
Citric acid—0.015 g
Water—68.385 g The size distribution of leukocytes thus obtained is shown in FIG. 3 (A).

COMPARATIVE EXAMPLE 1

Measurement of leukocytes was carried out in the same manner as described in Example 1 except that the conventional lysing reagent was employed against the same blood taken from patient 1. The result shown in FIG. 3 (B).

EXAMPLE 2

Figure 4A:
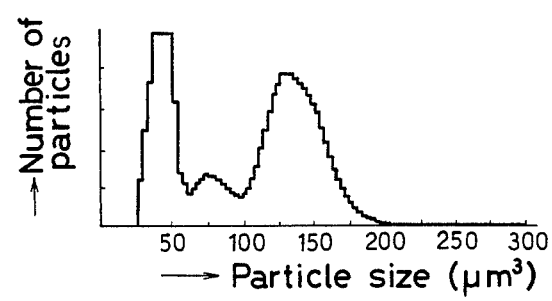
FIGS. 4 (A) and (B) are graphs showing the examination results in Example 2 and Comparative Example 2, respectively.
Figure 4B:
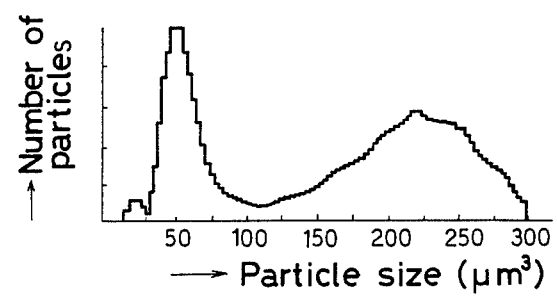

Measurement of leukocytes was carried out in the same manner as described in Example 1 except that blood taken from patient 2 was used as a sample, and that the lysing reagent having the following composition was used. The result is shown in FIG. 4 (A).
LTAC—28.5 g
MTAB—1.8 g
CTAC—1.8 g
Citric acid—0.015 g
Water—67.885 g

COMPARATIVE EXAMPLE 2

Measurement of leukocytes was carried out in the same manner as described in Example 2 except that the lysing reagent was the same as that of Comparative Example 1. The result is shown in FIG. 4 (B).

EXAMPLE 3

Figure 5A:
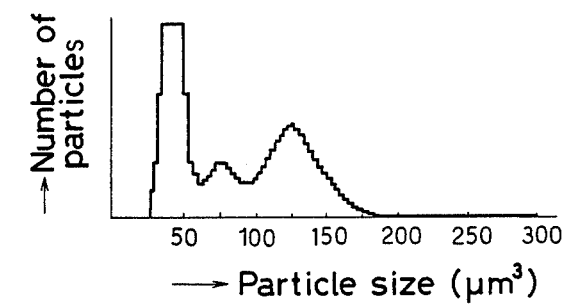
FIGS. 5 (A) and (B) are graphs showing the examination results in Examples and Comparative Example 3, respectively.
Figure 5B:
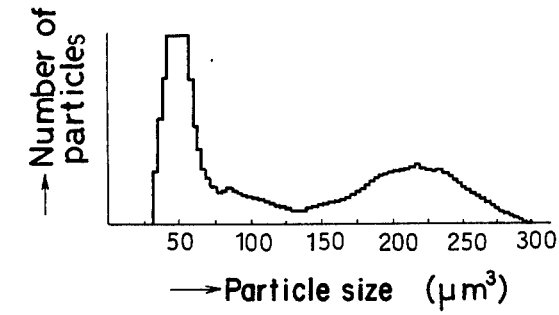
Figure 6:
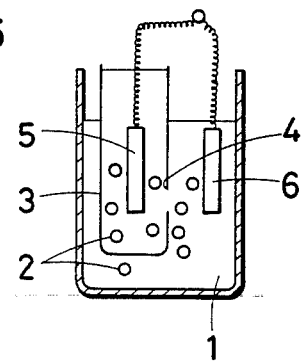
FIG. 6 is an explanatory view showing a mechanism for counting blood corpuscles in the conventional automatic blood-analysis instrument.
Figure 7:
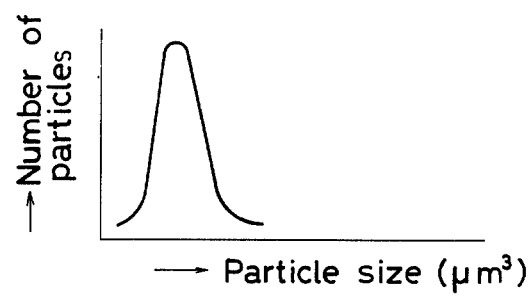
FIGS. 7 and 8 are graphs showing size distribution having one-peak fractionation and two-peaks fractionation.

Measurement of leukocytes was carried out in the same manner as described in Example 1 except that blood taken from patient 3 was used as a sample, and that the lysing reagent having the following composition was used. The result is shown in FIG. 5 (A).
LTAC—28.5 g
MTAB—3.5 g
Citric acid—0.015 g
Water—67.985 g

COMPARATIVE EXAMPLE 3

Measurement of leukocytes was carried out in the same manner as described in Example 3 except that the lysing reagent was the same as that of Comparative Example 1. The result is shown in FIG. 5 (B).

As obvious from these results, though the lysing reagents employed in each Example clearly show three-peaks fractionation, those employed in each comparative Example show only two-peaks fractionation.

What is claimed is:

1. A reagent for preparing cells for blood analysis comprising, as a lysing reagent for leukocyte count measurement, dodecyltrimethylammonium chloride; citric acid; and at least one member selected from the group consisting of tetradecyltrimethylammonium bromide and hexadecyltrimethylammonium chloride.

2. The reagent of claim 1 wherein said lysing reagent comprises 2.5 to 3.5 parts by weight of hexadecyltrimethylammonium chloride, 26 to 31.5 parts by weight of dodecyltrimethylammonium chloride and 0.01 to 0.02 parts by weight of citric acid.

3. The reagent of claim 1 wherein said lysing reagent comprises 1.6 to 2 parts by weight of hexadecyltrimethylammonium chloride, 1.6 to 2 parts by weight of tetradecyltrimethylammonium bromide, 26 to 31.5 parts by weight of dodecyltrimethylammonium chloride and 0.01 to 0.02 parts by weight of citric acid.

4. The reagent of claim 1 wherein said lysing reagent comprises 3 to 4 parts by weight of tetradecyltrimethylammonium bromide, 26 to 31.5 parts by weight of dodecyltrimethylammonium chloride and 0.01 to 0.02 parts by weight of citric acid.

* * * * *